United States Patent
Harper et al.

(10) Patent No.: US 9,283,001 B2
(45) Date of Patent: Mar. 15, 2016

(54) SYSTEMS FOR SPINAL STABILIZATION

(75) Inventors: Michael Harper, Pottstown, PA (US);
Milan George, King of Prussia, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 182 days.

(21) Appl. No.: 13/352,583

(22) Filed: Jan. 18, 2012

(65) Prior Publication Data

US 2013/0184762 A1 Jul. 18, 2013

(51) Int. Cl.
*A61B 17/88* (2006.01)
*A61B 17/70* (2006.01)

(52) U.S. Cl.
CPC .......... *A61B 17/7043* (2013.01); *A61B 17/7055* (2013.01); *A61B 17/7056* (2013.01)

(58) Field of Classification Search
CPC ........... A61B 17/7032; A61B 17/7002; A61B 17/7005; A61B 17/7085; A61B 17/704
USPC .................................................. 606/250–279
See application file for complete search history.

(56) References Cited

U.S. PATENT DOCUMENTS

| | | | |
|---|---|---|---|
| 4,274,401 A | 6/1981 | Miskew | |
| 4,505,268 A | 3/1985 | Sgandurra | |
| 5,102,412 A * | 4/1992 | Rogozinski | 606/86 A |
| 5,181,917 A * | 1/1993 | Rogozinski | 606/279 |
| 5,437,669 A * | 8/1995 | Yuan et al. | 606/278 |
| 5,507,747 A | 4/1996 | Yuan | |
| 5,688,273 A | 11/1997 | Errico | |
| 5,702,392 A * | 12/1997 | Wu et al. | 606/264 |
| 5,743,911 A | 4/1998 | Cotrel | |
| 6,858,029 B2 | 2/2005 | Yeh | |
| 7,338,490 B2 | 3/2008 | Olgivie et al. | |
| 8,083,780 B2 * | 12/2011 | McClellan et al. | 606/279 |
| 2003/0187437 A1 | 10/2003 | Ginsburg | |
| 2006/0241614 A1 * | 10/2006 | Bruneau et al. | 606/69 |
| 2007/0083199 A1 * | 4/2007 | Baccelli | 606/61 |
| 2007/0276384 A1 | 11/2007 | Spratt | |
| 2008/0058806 A1 | 3/2008 | Klyce | |

\* cited by examiner

*Primary Examiner* — Mary Hoffman
*Assistant Examiner* — Tara R Carter

(57) ABSTRACT

Systems, devices and methods related to spinal stabilization are provided. A system can comprise a plurality of cross-links. Each of the cross-links can include a central rod holder that extends substantially along a mid-line of the spine and a pair of extension members extending from the central rod holder. The extension members can be secured to a vertebral body via a fixation device, such as a spinal screw or a hook member having serrations and/or side-cuts. One or more rod members can be extended across the central rod holders of the cross-links, thereby forming a stable spinal stabilization system providing bilateral stress distribution across different levels of the spine.

19 Claims, 6 Drawing Sheets

SYSTEMS FOR SPINAL STABILIZATION

FIELD OF THE INVENTION

The present application is generally directed to orthopedic stabilization systems, and in particular, to central stabilization systems including rod members and fixation members.

BACKGROUND OF THE INVENTION

Many types of spinal irregularities cause pain, limit range of motion, or injure the nervous system within the spinal column. These irregularities can result from, without limitations, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to an elongate rod that generally extends in the direction of the axis of the spine.

Treatment of these spinal irregularities can involve using a system of screws and rods to attain stability between spinal segments. Instability in the spine can create stress and strain on neurological elements, such as the spinal cord and nerve rods. In order to correct this, implants of certain stiffness can be implanted to restore the correct alignment and portion of the vertebral bodies. In many cases, these implants can help restore spinal elements to a pain free situation, or at least may help reduce pain or prevent further injury to the spine.

Accordingly, there is a need for improved systems involving screws and rods for spinal stabilization.

SUMMARY OF THE INVENTION

Various systems, devices and methods related to spinal stabilization are provided. In some embodiments, a method for spinal stabilization comprises providing a plurality of cross-links, each of the cross-links including a central rod holder and first and second extension members extending therefrom. Each of the cross-links can be operably attached to a vertebral body by attaching a first extension member to a first fixation member and attaching a second extension member to a second fixation member. The first fixation member and the second fixation member can be attached to the vertebral body. Once two or more cross-links are installed, a rod member can be secured to the central rod holders of the multiple cross-links, thereby creating a stabilized system across multiple levels of the spine.

In some embodiments, a method for spinal stabilization comprises providing one or more cross-links configured to extend across a mid-line of a spine. A first portion of a cross-link can be attached to a first fixation member, wherein the first fixation member is attached to a vertebral body. A second portion of the cross-link can be attached to a second fixation member, wherein the second fixation member is attached to a vertebral body. At least one of the first fixation member and the second fixation member is a hook member having a pair of arms and a mouth with serrations.

In some embodiments, a method for spinal stabilization comprises providing one or more cross-links configured to extend across a mid-line of a spine. A first portion of a cross-link can be attached to a first fixation member, wherein the first fixation member is attached to a vertebral body. A second portion of the cross-link can be attached to a second fixation member, wherein the second fixation member is attached to a vertebral body. At least one of the first fixation member and the second fixation member is a hook member having a pair of arms forming a channel, wherein at least one of the arms includes a side-cut formed therein.

BRIEF DESCRIPTION OF THE DRAWINGS

The invention will be more readily understood with reference to the embodiments thereof illustrated in the attached figures, in which.

DETAILED DESCRIPTION OF THE ILLUSTRATED EMBODIMENTS

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

The present application is generally directed to orthopedic stabilization systems, and in particular, to central stabilization systems including rod members and fixation members.

Figure 1:
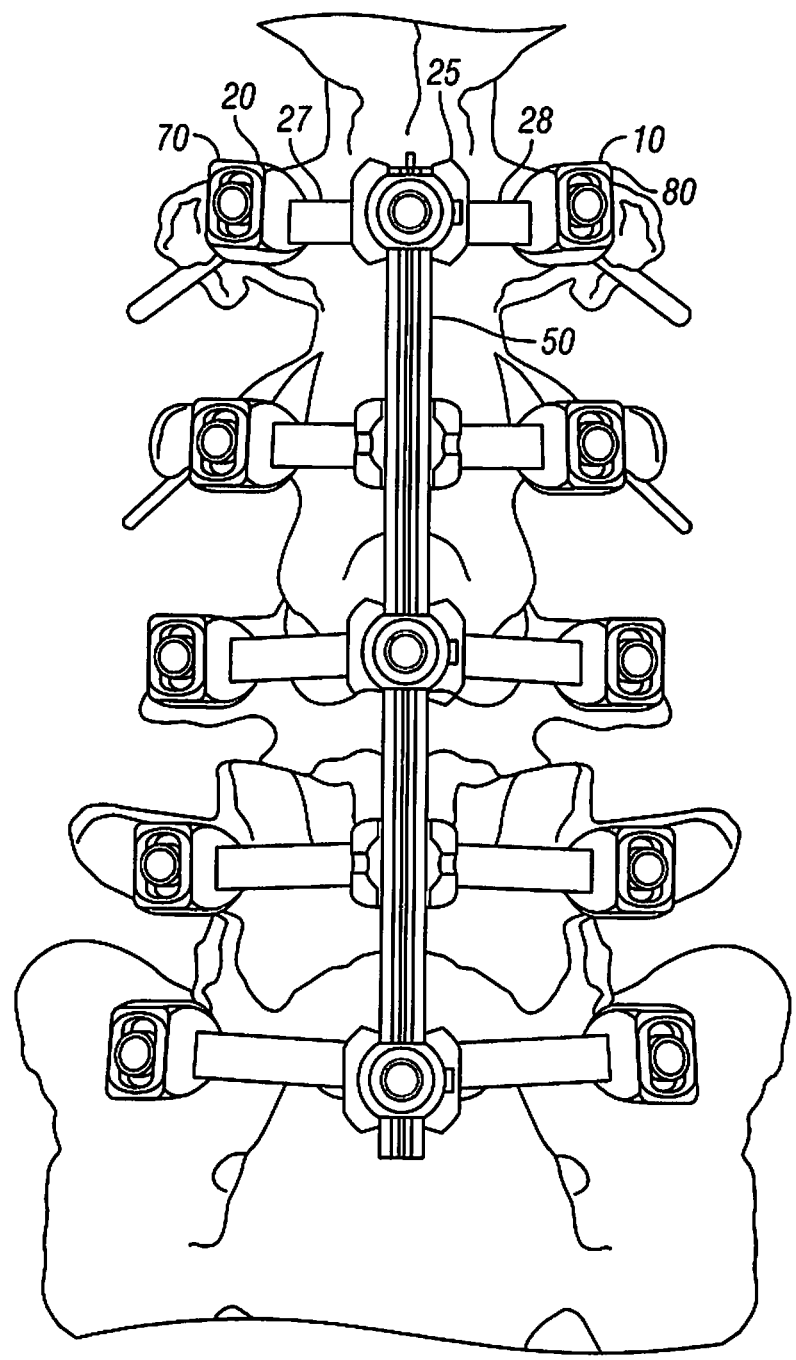
FIG. 1 is a top view of a central rod system in use according to some embodiments.

FIG. 1 is a top view of a central rod system in use with a spine according to some embodiments. The central rod system 10 comprises a plurality of cross-links 20 that extend along different spinal levels. Each of the cross-links in the system (shown individually in FIGS. 3 and 4), advantageously include a central rod holder 25 that is designed to hold one or more rod members across multiple spinal levels. As shown in FIG. 1, one or more central rods 50 can extend through the central rod holders 25 of the cross-links 20, thereby helping to create a stable system to ease complex deformity correction. In some embodiments, the central rods 50 extend over reduced or removed spinal processes such that they are positioned substantially through a center of the spine.

Each of the central rod holders 25 also includes a pair of extension members 27, 28 that extend outwardly from the central rod holder 25. Each of the extension members 27, 28 can be attached to a fixation element, such as such as a screw. As shown in FIG. 1, extension member 27 is attached to fixation element 70, while extension member 28 is attached to fixation element 80. The fixation elements 70, 80 advantageously help to secure the extension members 27, 28 of the central rod holder 25 bilaterally on opposite sides of a midline of the spine. More details with respect to the central rod holder 25 are discussed below.

Figure 2:
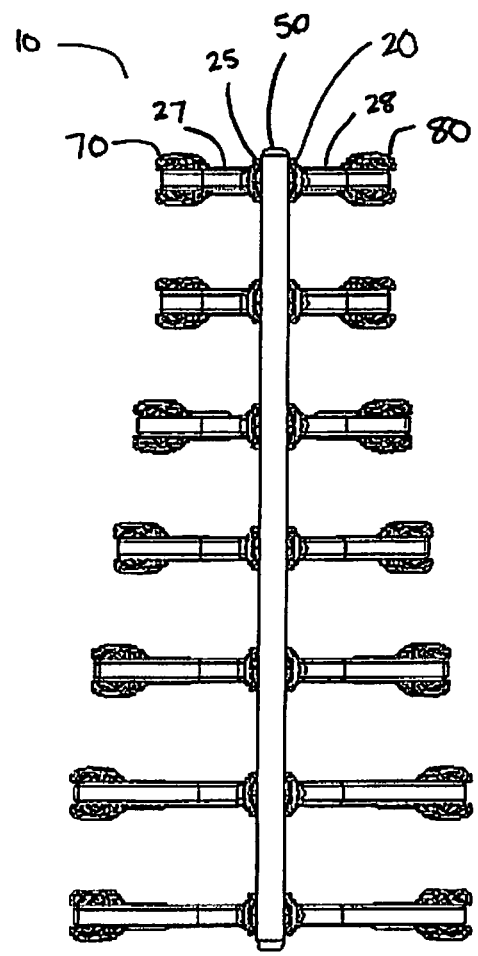
FIG. 2 is a top view of a central rod system according to some embodiments.

FIG. 2 is a top view of a central rod system according to some embodiments. The central rod system 10 includes seven cross-links 20, each having a central rod holder 25 and a pair of extension members 27, 28 extending outwardly therefrom. In some embodiments, different extension members 27, 28 in a central rod system can have different lengths to advantageously accommodate different levels of the spine. For example, as shown in FIGS. 1 and 2, extension members 27, 28 found on a higher portion of the spine (e.g., in the lumbar region) can be shorter in length than extension members found in a lower portion of the spine (e.g., the sacrum). In some embodiments, the central rod system include extension members 27, 28 that increase in length from a higher portion to a lower portion of the spine.

Figure 3:
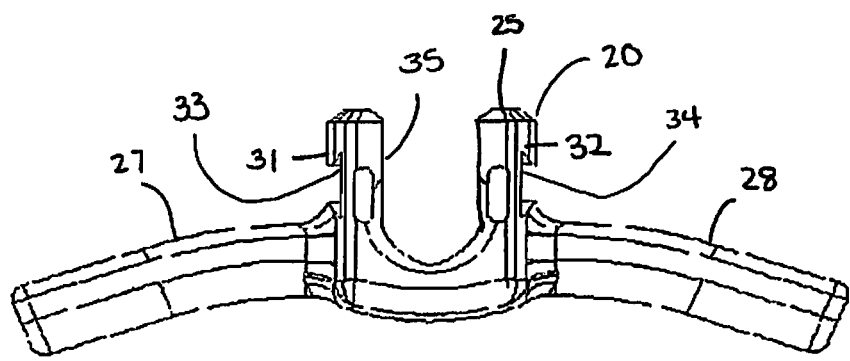
FIG. 3 is a front view of a cross-link of a central rod system according to some embodiments.

FIG. 3 is a front view of a cross-link of a central rod system according to some embodiments. As noted above, the cross-link 20 includes a central rod holder 25 with a pair of extension members 27, 28 extending therefrom. In some embodiments, the central rod holder 25 comprises an open or closed connector head that can be offered in a variety of configurations, including but not limited to, a monomial head, uniplanar head, polyaxial head, spinning head and a sliding head.

The central rod holder 25 comprises a pair of arms 31, 32 that form sidewalls of a U-shaped channel 35. In some embodiments, the arms 31, 32 each include recessed portions 33, 34, which can be engaged by an insertion instrument or sleeve to deliver the cross-link to a desired location adjacent a spine. The U-shaped channel 35 is configured to receive one or more rod members that connect across multiple levels of the spine to provide spine stabilization.

Figure 4:
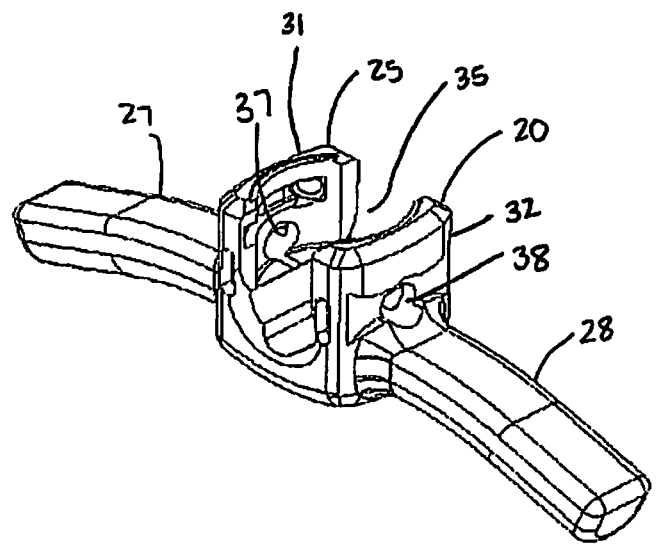
FIG. 4 is a top perspective view of a cross-link of a central rod system according to some embodiments.

FIG. 4 is a top perspective view of a cross-link of a central rod system according to some embodiments. From this view, more details of the arms 31, 32 of the central rod holder 25 are visible. The arms 31, 32 each include individual apertures 37, 38. In some embodiments, the individual apertures 37, 38 can receive a part of an insertion instrument or sleeve, such as a tab member, to assist in securing the instrument to the arms during delivery of the cross-link.

Figure 5:
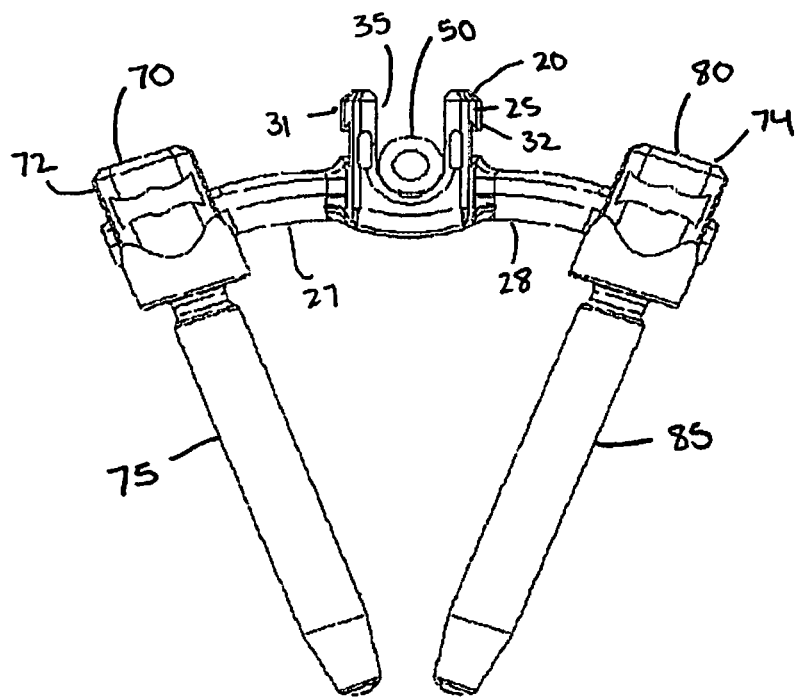
FIG. 5 is a front view of a cross-link of a central rod system having a rod therein according to some embodiments.

FIG. 5 is a front view of a cross-link of a central rod system having a rod therein according to some embodiments. The rod 50 is positioned within the central rod holder 25 of the cross-link 20.

In addition, the extension members 27, 28 of the cross-link are operatively attached to fixation members 70, 80. Each of the fixation members 70, 80 includes a head member 72, 74 for receiving extension members 27, 28 therein. The head members 72, 74 are connected to shafts 75, 85 that can be inserted into the spine for fixation.

Methods related to the central rod systems discussed above are now provided. In some embodiments, a surgical procedure for installing a central rod system involves removing all or a portion of one or more spinal processes. In other embodiments, the spinal processes remain intact while components of a central rod system curve or work around the spinal processes. In some embodiments, once the spinal processes are removed, a plurality of cross-links are provided. Each of the cross-links includes a central rod holder and first and second extension members extending therefrom. The cross-links can be installed individually to a vertebral body by securing the first extension member to the vertebral body via a first fixation member (e.g., a screw or a hook) and by securing the second extension member to the vertebral body via a second fixation member (e.g., a screw or a hook). Locking mechanisms, such as locking caps, can be provided to secure the extension members to the fixation members.

Figure 6A:
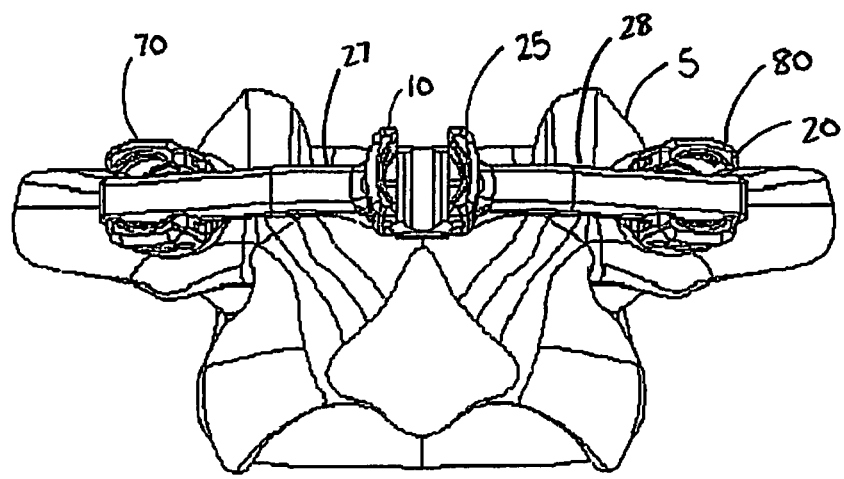
FIG. 6A is top view of a cross-link of a central rod system attached to a vertebral body according to some embodiments.
Figure 6B:
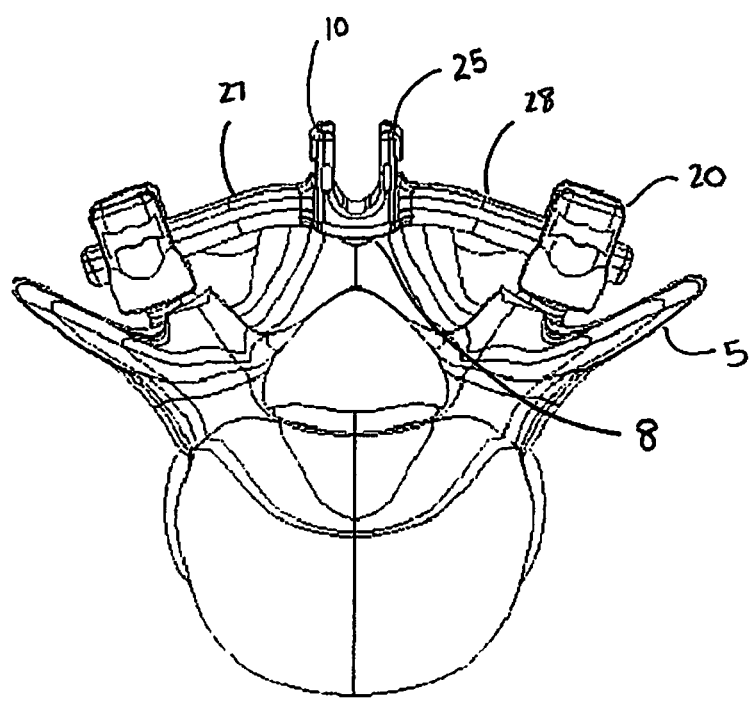
FIG. 6B is a front view of a cross-link of a central rod system attached to a vertebral body according to some embodiments.

FIGS. 6A and 6B illustrate a single cross-link member 20 attached to a vertebral body 5. The cross-link member 20 has a central rod holder 25 and extension members 27, 28 extending therefrom that are secured to a vertebral body via fixation members 70, 80. From the view in FIG. 6B, one can see how the cross-link member 20 is attached over a modified spinous process 8. One or more cross-link members can be attached as shown in these figures.

During surgery, one or more cross-links can be installed such that their central rod holders align substantially along a mid-plane of the spine and/or over the modified spinal processes. After installing a plurality of cross-links, one or more rod members can be inserted through the central rod holders and secured therein (e.g., via a locking mechanism or cap). The one or more rod members extend across multiple levels of the spine, thereby creating a stable, central rod system across multiple levels.

By providing a central rod system as discussed above, a number of advantages are achieved for spinal stabilization. Among the advantages include bilateral stress distribution to alleviate unilateral stress concentrations during deformity correction; centralized sagital plant correction; reduced rod bending in planar operations (e.g., lordosis and kyphosis); a centralized rotation axis allowing for a more intuitive local vertebral rotation; and a system that can be utilized to accommodate growing rod applications.

In addition or instead of the components of the central rod system discussed above, other components can be used. For example, a variety of different hook members can be used instead of the pedicle screws 70, 80 shown above for attachment to a vertebral body. While such hook members can be used as part of a central rod system as discussed above, they can also be used in other spine systems that are different from the central rod system. Novel hook members are discussed below.

Figure 7:
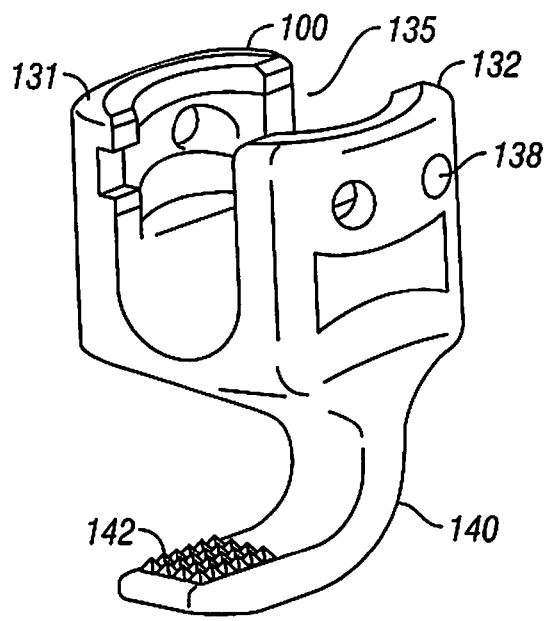
FIG. 7 is a perspective view of a hook member having serrations according to some embodiments.

FIG. 7 is a perspective view of a hook member having serrations according to some embodiments. The hook member 100 includes a pair of arms 131, 132 that form a channel 135 for receiving a rod member therein. The arms can include one or more apertures 138 formed thereon, which can be grasped by an insertion or delivery instrument. The bottom of the channel 135 can sweep downwardly to form a mouth 140. The mouth 140 of the hook member 100 can advantageously be used to grasp a bone member. Advantageously, the serrations 142 provide the hook member 100 with additional fixation in both translational and rotational planes such that the likelihood of back out or migration of the hooks is reduced.

In some embodiments, the mouth 140 of the hook member 100 includes a plurality of serrations 142 thereon. The serrations 142 advantageously provide multiple points of contact that dig into bone when the hook member 100 is press-fitted onto bone.

Figure 8:
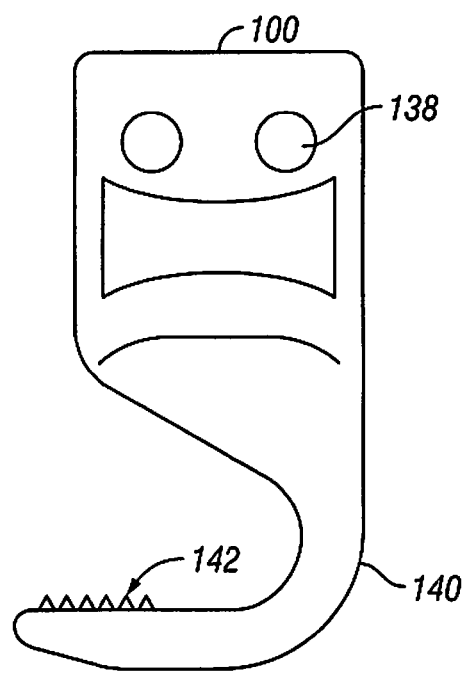
FIG. 8 is a side view of a hook member having serrations according to some embodiments.

FIG. 8 is a side view of a hook member having serrations according to some embodiments. From this view, the geometry of the serrations 142 can be seen. As shown in FIG. 8, the serrations 142 can be evenly spaced, and can resemble triangular or pyramidal teeth. In other embodiments, the hook member 100 can include serrations or frictional contact-surfaces with other shapes, including saw-tooth forms, ridges and rounded bumps.

Figure 9:
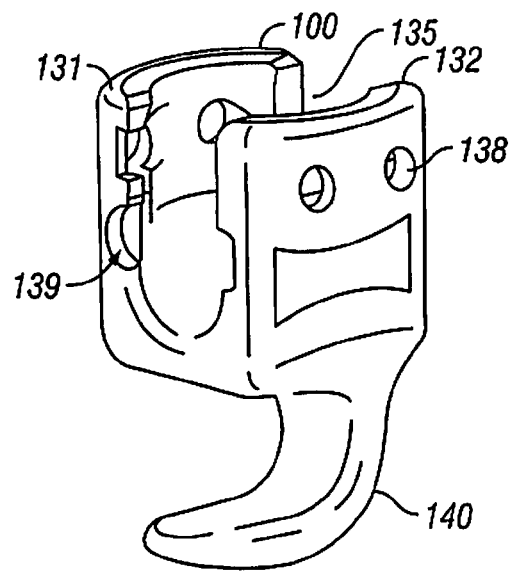
FIG. 9 is a perspective view of a hook member having side-cuts according to some embodiments.

FIG. 9 is a perspective view of an alternative hook member that can be used alone or in combination with a spinal system, such as the central rod system discussed above. Like the hook member 100 in FIG. 8, the hook member in FIG. 9 includes a pair of arms 131, 132 that form a channel 135 for receiving a rod member therein, as well as a mouth portion 140 for attachment to a vertebral body. The arms 131, 132 can include one or more apertures 138 for gripping by an insertion instrument. Advantageously, the arms 131, 132 of the hook member 100 can also include side-cuts 139. These side-cuts advantageously provide additional points of contact with respect to instruments that hold it while the hook is press-fitted into bone. In other words, the hook member 100 has additional fixation points for the instrument to engage with, in both translational and rotational planes, thereby reducing the chance of hook slippage during implantation.

Figure 10:
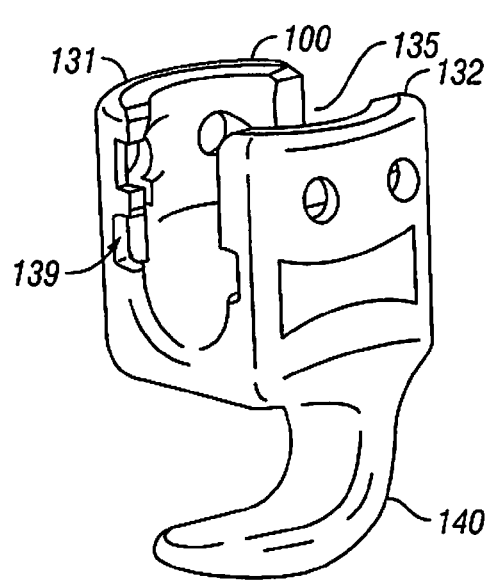
FIG. 10 is a perspective view of a hook member having alternative side-cuts according to some embodiments.
Figure 11:
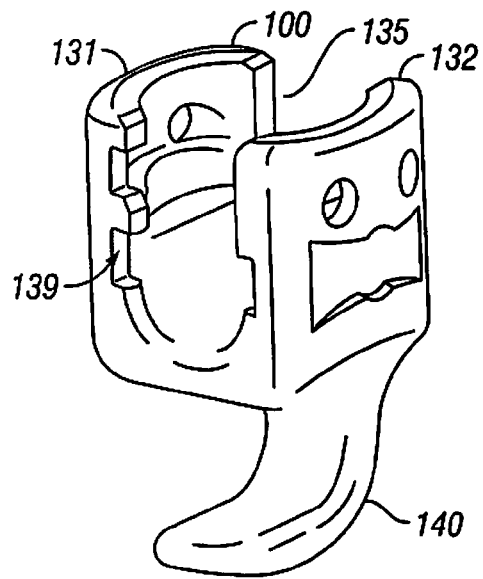
FIG. 11 is a perspective view of a hook member having alternative side-cuts according to some embodiments.

FIGS. 9-11 each show hook members 100 having side-cuts 139 with different shapes and geometries. In FIG. 9, the hook member 100 includes a side-cut 139a that is rounded and appears as a semi-circle. In FIG. 10, the hook member 100 includes a side-cut 139b that appears as a rectangular recess formed in the arms 131, 132 of the hook member 100. In FIG. 11, the hook member 100 includes a side-cut 139 that is completely rectangular cut-out and not simply a recess. Accordingly, the hook members 100 have a number of differently shaped and oriented side-cuts that be gripped by an insertion instrument.

While the invention herein disclosed has been described by means of specific embodiments and applications thereof, numerous modifications and variations can be made thereto by those skilled in the art without departing from the scope of the invention.

What is claimed is:

1. A method for spinal stabilization comprising:
   providing a plurality of cross-links, each of the cross-links including a central rod holder and first and second extension members extending therefrom;
   operably attaching each of the cross-links to a vertebral body, whereby attachment comprises:
      attaching the first extension member to a first fixation member, wherein the first fixation member is attached to the vertebral body, wherein the first fixation member comprises a pair of upwardly extending arms for receiving a rod therein and a downwardly extending mouth having a curved portion that transitions into a flat portion, wherein at least one of the upwardly extending arms includes a first end and a second end, an outside surface that extends between the first end and the second end, an inside surface configured to face the rod, an aperture extending from the outside surface to the inside surface, and a side-cut, wherein the side-cut is formed on at least one of the first end and the second end and opens into a channel formed by the pair of upwardly extending arms;
      and attaching the second extension member to a second fixation member, wherein the second fixation member is attached to the vertebral body; and
   securing a rod member to the central rod holder of two or more cross-links, thereby creating a stabilized system across multiple levels of the spine
   wherein each one of the at least one of the upwardly extending arms include recessed portions that are configured to engage with a insertion instrument
   wherein the aperture of each of the upwardly extending arms are positioned in the recessed portions of the upwardly extending arms.

2. The method of claim 1, wherein the central rod holder comprises a pair of arms forming a channel therein.

3. The method of claim 1, wherein a width of the extension members of a first cross-link is different from a width of the extension members of a second cross-link.

4. The method of claim 1, wherein providing a plurality of cross-links comprises providing at least five cross-links.

5. The method of claim 4, wherein at least one of the cross-links is configured to attach to a sacrum.

6. The method of claim 1, wherein the first fixation member is attached to a pedicle.

7. The method of claim 6, wherein the second fixation member is attached to a pedicle.

8. The method of claim 1, wherein the first fixation member further comprises a second side cut formed adjacent to the side cut, wherein the second side cut also opens into the channel formed by the pair of upwardly extending arms.

9. A method for spinal stabilization comprising:
   providing one or more cross-links configured to extend across a mid-line of a spine;
   attaching a first portion of a cross-link to a first fixation member, wherein the first fixation member is attached to a vertebral body, wherein the first fixation member comprises a pair of upwardly extending arms for receiving a rod therein and a downwardly extending mouth having a curved portion that transitions into a flat portion, wherein at least one of the upwardly extending arms includes first end and a second end, an outside surface that extends between the first end and the second end, an inside surface configured to face the rod, an aperture extending from the outside surface to the inside surface, and a side-cut, wherein the side-cut is formed on at least one of the first end and the second end and opens into a channel formed by the pair of upwardly extending arms; and
   attaching a second portion of the cross-link to a second fixation member, wherein the second fixation member is attached to a vertebral body
   wherein each one of the at least one of the upwardly extending arms include recessed portions that are configured to engage with a insertion instrument
   wherein the aperture of each of the upwardly extending arms are positioned in the recessed portions of the upwardly extending arms.

10. The method of claim 9, wherein at least one of the cross-links comprises a central rod holder.

11. The method of claim 10, wherein the central rod holder includes a pair of extension members extending therefrom.

12. The method of claim 9, wherein the flat portion of the mouth includes serrations, wherein the serrations are pyramidal shaped.

13. The method of claim 9, wherein the flat portion of the mouth includes serrations, wherein the serrations are sawtooth shaped.

14. The method of claim 9, wherein the first fixation member comprises a hook member and the second fixation member comprises a screw.

15. A method for spinal stabilization comprising:
   providing one or more cross-links configured to extend across a mid-line of a spine;
   attaching a first portion of a cross-link to a first fixation member, wherein the first fixation member is attached to a vertebral body, wherein the first fixation member comprises a pair of upwardly extending arms for receiving a rod therein and a downwardly extending mouth having a curved portion that transitions into a flat portion, wherein at least one of the upwardly extending arms includes a first end and a second end, an outside surface that extends between the first end and the second, an inside surface configured to face the rod, an aperture extending from the outside surface to the inside surface, and a side-cut, wherein the side-cut is formed on at least one of the first end and the second end and opens into a channel formed by the pair of upwardly extending arms; and attaching a second portion of the cross-link to a second fixation member, wherein the second fixation member is attached to a vertebral body;

wherein at least one of the first fixation member and the second fixation member is a hook member having a pair of arms forming a channel wherein each one of the at least one of the upwardly extending arms include recessed portions that are configured to engage with a insertion instrument wherein the aperture of each of the upwardly extending arms are positioned in the recessed portions of the upwardly extending arms.

16. The method of claim 15, wherein the first fixation member further comprises a second side-cut formed adjacent to the side-cut, wherein the second side-cut also opens into a channel formed by the pair of upwardly extending arms.

17. The method of claim 15, wherein the side-cut comprises a semi-circle cut-out.

18. The method of claim 15, wherein at least one of the cross-links comprises a central rod holder.

19. The method of claim 15, wherein the first fixation member comprises a hook member and the second fixation member comprises a screw.

* * * * *